(12) United States Patent
Macy et al.

(10) Patent No.: US 8,627,970 B2
(45) Date of Patent: Jan. 14, 2014

(54) CLOSURE WITH SHIELD, STOPPER, AND PUSHER, AND METHOD FOR MAKING THE SAME

(75) Inventors: Johnathan Macy, Virginia Beach, VA (US); Michael Bucholtz, Ballston Spa, NY (US)

(73) Assignee: Capitol Medical Devices, Inc., Auburn, AL (US)

( * ) Notice: Subject to any disclaimer, the term of this patent is extended or adjusted under 35 U.S.C. 154(b) by 0 days.

(21) Appl. No.: 13/520,037

(22) PCT Filed: Jan. 6, 2011

(86) PCT No.: PCT/US2011/020357
§ 371 (c)(1),
(2), (4) Date: Sep. 21, 2012

(87) PCT Pub. No.: WO2011/085089
PCT Pub. Date: Jul. 14, 2011

(65) Prior Publication Data
US 2013/0140262 A1    Jun. 6, 2013

Related U.S. Application Data

(60) Provisional application No. 61/292,533, filed on Jan. 6, 2010.

(51) Int. Cl.
*B65D 41/28* (2006.01)
*B65D 51/18* (2006.01)
*B65D 39/16* (2006.01)

(52) U.S. Cl.
CPC ............... *B65D 39/16* (2013.01); *B65D 41/28* (2013.01); *B65D 51/18* (2013.01)
USPC ........ 215/296; 215/228; 220/285; 220/254.8; 220/259.3

(58) Field of Classification Search
USPC ................. 215/296, 295, 200, 364, 356, 355; 220/285, 284, 260, 254.8, 254.1, 220/259.3, 256.1, 212, 200
IPC ............ B65D 41/28,41/02, 41/58, 41/32, 51/18
See application file for complete search history.

(56) References Cited

U.S. PATENT DOCUMENTS 5,361,921 A    11/1994  Burns
5,718,348 A *  2/1998  Manera ......................... 215/249
(Continued)

FOREIGN PATENT DOCUMENTS

EP        0366617        5/1990

OTHER PUBLICATIONS

International Search Report and Written Opinion for International Patent Application No. PCT/US2011/020357 mailed Sep. 7, 2011.
(Continued)

*Primary Examiner* — Robert J Hicks
(74) *Attorney, Agent, or Firm* — McAndrews, Held & Malloy, Ltd.

(57) ABSTRACT

A closure is shown for closing an opening of a vessel. The closure includes a stopper, a shield, and a pusher. The stopper seats at least partially within the vessel opening. The shield includes a recess configured to receive the stopper and at least partially defined by the inner surface of a skirt. The skirt is positioned outside the generally cylindrical neck of the vessel when the stopper is seated in the vessel opening. The pusher extends into the recess of the shield. The pusher is configured to push the stopper out of the opening when the shield is withdrawn axially, as when removing the closure from the opening. A method of assembling a closure is also shown, in which the pusher is positioned to push the stopper out of the opening when the shield is withdrawn axially from the vessel opening.

19 Claims, 5 Drawing Sheets

(56) References Cited

U.S. PATENT DOCUMENTS

| | | | |
|---|---|---|---|
| 6,602,206 B1 | 8/2003 | Niermann et al. | |
| 2007/0272645 A1* | 11/2007 | Ito et al. | 215/11.1 |
| 2007/0272648 A1* | 11/2007 | Hamamoto et al. | 215/277 |
| 2009/0308184 A1 | 12/2009 | Alex et al. | |

OTHER PUBLICATIONS

PCT, Notification Concerning Transmittal of International Preliminary Report on Patentability, in international application No. PCT/US2011/020357, dated Jul. 19, 2012.

* cited by examiner

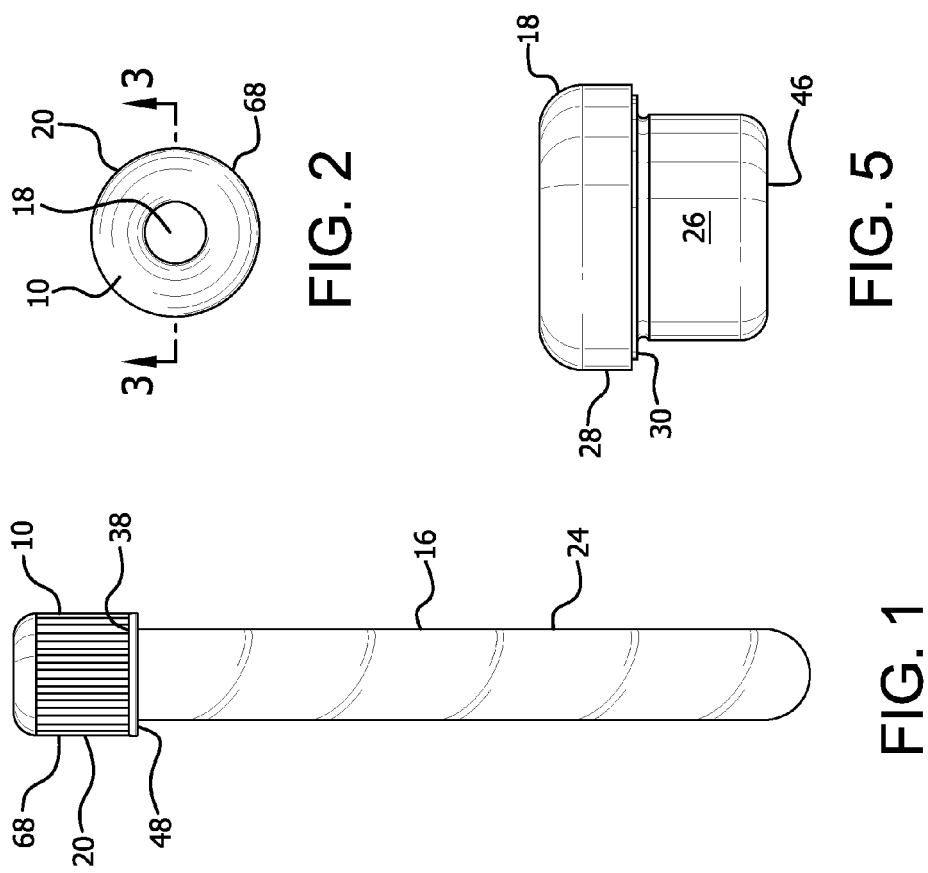

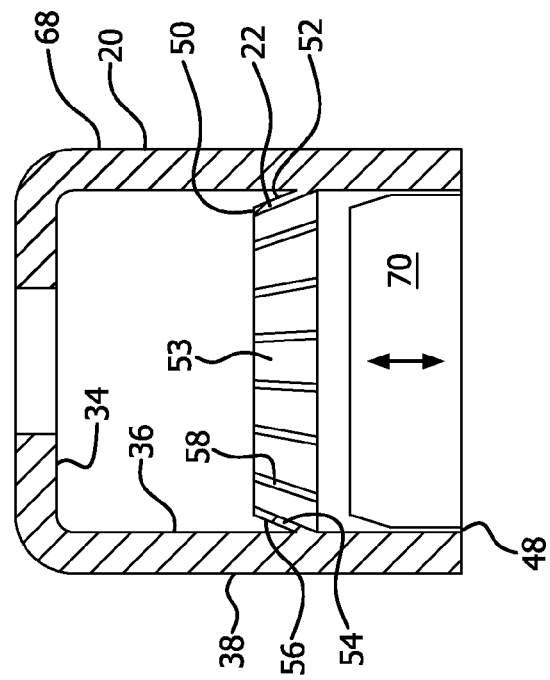
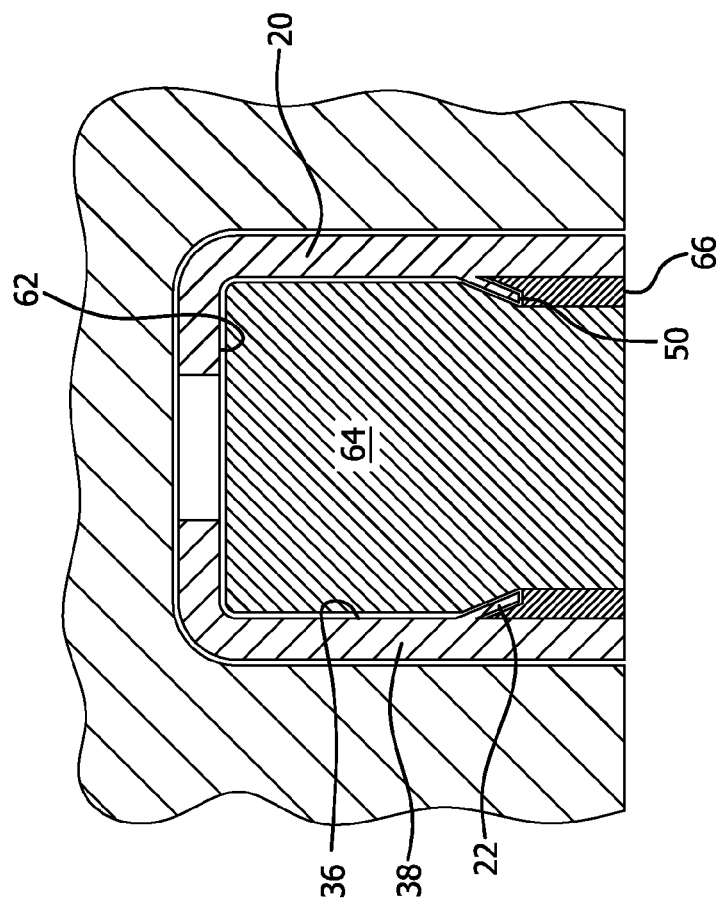

CLOSURE WITH SHIELD, STOPPER, AND PUSHER, AND METHOD FOR MAKING THE SAME

RELATED APPLICATION

This application is a 371 National Phase filing of International Patent Application Serial No. PCT/US2011/020357 filed Jan. 6, 2011, which claims priority benefit of U.S. Provisional Patent Application Ser. No. 61/292,533 filed Jan. 6, 2010. Both applications are incorporated herein by reference in their entirety.

BACKGROUND OF THE INVENTION

The invention relates in general to a closure for a vessel opening, and more particularly to a two-part closure having a stopper and a shield. A known type of closure of this general type is shown in U.S. Pat. No. 4,741,446.

BRIEF SUMMARY OF THE INVENTION

An aspect of the invention is a closure for an opening of a generally cylindrical neck of a vessel. The closure includes a stopper, a shield, and a pusher. The stopper is configured to seat at least partially within the vessel opening. The shield includes a recess configured to receive at least a portion of the stopper. The recess is at least partially defined by the inner surface of a skirt. The skirt is configured to be positioned outside the generally cylindrical neck of the vessel when the stopper is seated in the vessel opening.

A pusher extends radially from the inner surface of the skirt into the recess of the shield. The pusher has a distal portion, with respect to the inner surface of the skirt. The pusher is movable between a first position extending axially outward from the inner surface of the skirt and a second position extending axially inward from the inner surface of the skirt.

The distal portion of the pusher engages the stopper. The pusher is configured to push the stopper out of the opening when the shield is withdrawn axially from the generally cylindrical neck of the vessel, for example when removing the closure from the vessel opening.

Another aspect of the invention is a method of assembling a closure configured to close the vessel opening. The method can be carried out as follows.

A stopper, shield, and pusher are provided. The stopper is configured to be seated at least partially within the vessel opening. The shield has a recess configured to at least partially receive the stopper. The recess is at least partially defined by the inner surface of a skirt. The recess has an opening sized to pass at least a portion of the stopper. The pusher is provided within the shield. The pusher has a distal portion extending radially into the recess from the inner surface of the skirt.

The pusher distal portion is initially located in a first position extending axially outward from the inner surface of the skirt. The pusher distal portion is then displaced to a second position extending axially inward from the inner surface of the skirt.

The stopper is inserted into the recess of the shield to a seated position. When the stopper is seated in the recess, the pusher engages the stopper and is positioned to push the stopper out of the opening when the shield is withdrawn axially from the vessel opening.

Other aspects of the invention are disclosed or will be apparent to those skilled in the art upon review of the following description and claims.

BRIEF DESCRIPTION OF SEVERAL VIEWS OF THE DRAWINGS

FIG. 1 shows a side elevation view of an embodiment of the disclosed technology.

FIG. 2 shows a plan view of the embodiment of FIG. 1.

FIG. 5 shows an isolated elevation view of the stopper of the embodiment of FIG. 1.

FIG. 6 shows an isolated sectional view like that of FIG. 3 of the shield of the embodiment of FIG. 1, as molded in an embodiment of the invention.

FIG. 7 shows a view of the shield of FIG. 6 in a closed injection mold in which it optionally can be formed.

FIG. 9 is an isolated cutaway view of a pusher according to an alternate embodiment of the disclosed technology.

The following reference characters are used in this specification. The same reference characters indicate corresponding parts in the several views.

Figure 3:
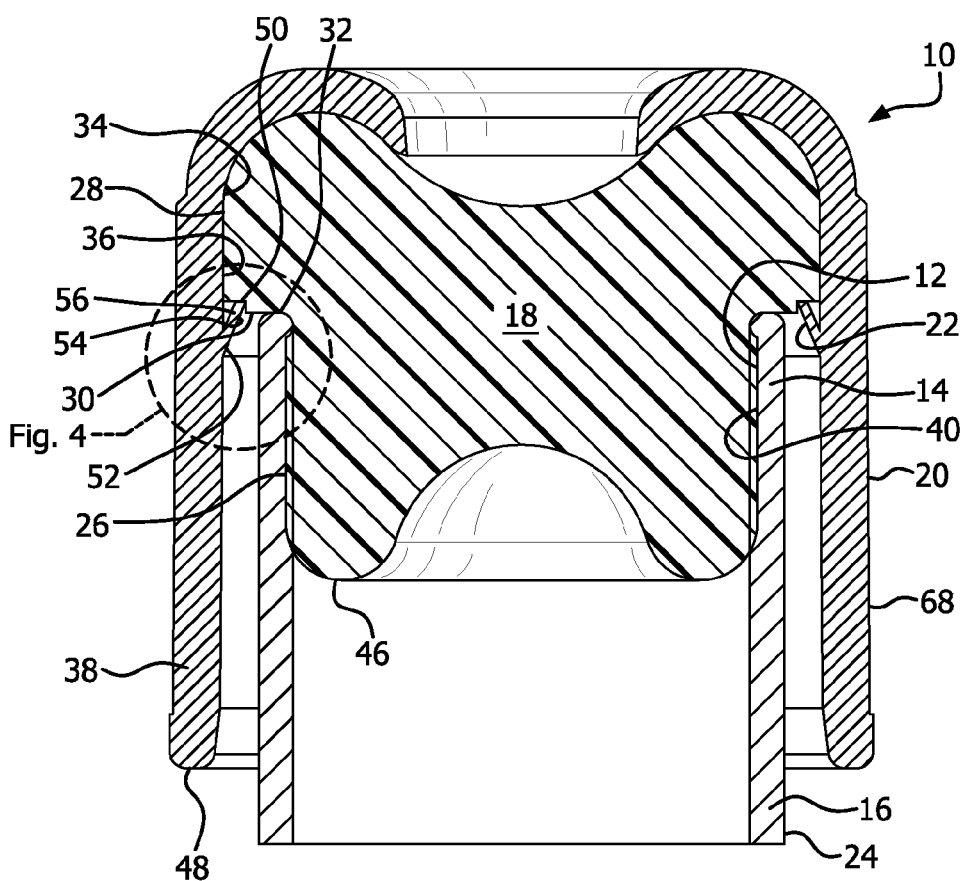
FIG. 3 shows a section taken along section lines 3-3 of FIG. 2, with the lower portion of the tube cut away.

| | |
|---|---|
| 10 | Closure |
| 12 | Opening (of 14) |
| 14 | Neck (of 16) |
| 16 | Vessel |
| 18 | Stopper |
| 20 | Shield |
| 22 | Pusher |
| 24 | Body (of 16) |
| 26 | Body portion (of 18) |
| 28 | Head portion (of 18) |
| 30 | Abutment (of 18) |
| 32 | Lip (of 14) |
| 34 | Recess (of 20) |
| 36 | Inner surface (of 38) |
| 38 | Skirt (of 20) |
| 40 | Inner surface (of 14) |
| 42 | Thread (of 38) |
| 44 | Thread (of 14) |
| 46 | Lower end (of 18) |
| 48 | Opening (of 20) |
| 50 | Distal portion (of 22) |
| 52 | Proximal portion (of 22) |
| 53 | Web (of 22) |
| 54 | Outer surface (of 22) |
| 56 | Inner surface (of 22) |
| 58 | Raised projection (of 56) |
| 62 | Mold cavity |
| 64 | Inner core |
| 66 | Outer core |
| 68 | Exterior (of 20) |
| 70 | Tool |
| 80 | Step |

DETAILED DESCRIPTION OF THE INVENTION

Referring to an embodiment shown in FIGS. 1-7, a closure generally indicated as 10 is shown that is useful for closing an opening 12 of a generally cylindrical neck 14 of a vessel 16. The closure 10 includes a stopper 18, a shield 20, and a pusher 22.

The vessel 16 illustrated in the Figures is a medical sample collection tube, one example of which is an evacuated blood collection tube, described for example in connection with FIG. 3 of U.S. Pat. No. 4,741,446. In such a vessel, having in general the shape of a test tube, the neck 14 has substantially the same diameter as the body 24 of the vessel. A jar is another example of a vessel having a neck that is the same or nearly the same diameter as the body of the vessel. A neck having a smaller diameter than the body of the vessel is also contemplated, for example, a bottle. A neck having a larger diameter than the body of the vessel is also contemplated.

The stopper 18 is configured to seat at least partially within the vessel 16 opening 12 to isolate the contents of the vessel 16 from the ambient environment. The stopper 18 includes a body portion 26 configured to seat at least partially within the opening 12. The stopper 18 as illustrated in FIG. 3 includes a head portion 28 secured to (and as illustrated integral with) the body portion 26. The head portion 28 is configured to extend at least partially outside the opening 12 when the body portion is seated at least partially within the opening 12.

Figure 4:
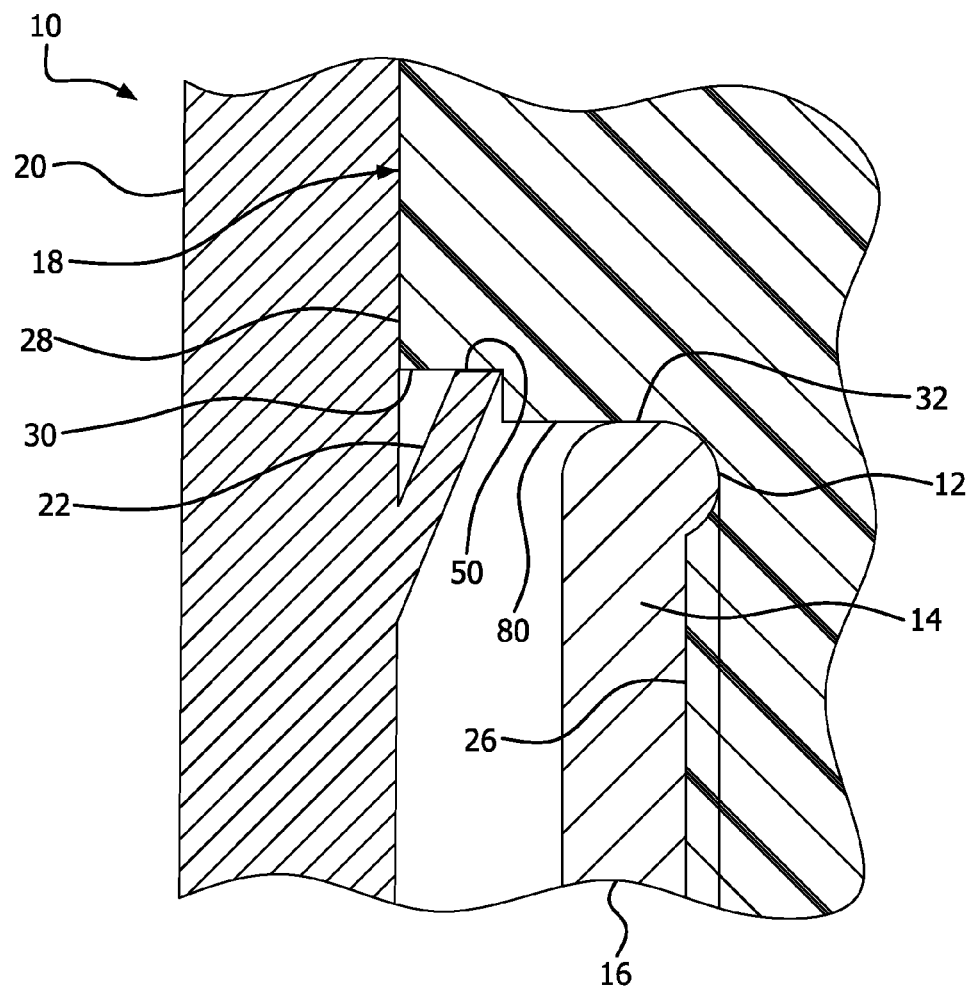
FIG. 4 shows an enlarged detail view of FIG. 3.

As shown in FIGS. 3 and 4, the head portion 28 can include a stopper abutment 30 extending radially outward from the body portion 26 of the stopper 18. The pusher 22 of the shield 20 bears against the stopper abutment 30 to assist in pushing the stopper 18 out of the opening 12. Although in an alternative embodiment the stopper abutment 30 could abut the lip 32 of the neck 14, this is not required, and the abutment 30 alternatively can be out of contact with the lip 32. The stopper abutment 30 can be a circumferentially extending flange, as illustrated in FIGS. 3 and 4. In the illustrated embodiment a step 80 is provided to prevent any portion of the pusher 22 from sliding radially inward of the abutment 30. The step 80 of this embodiment optionally can act as a stop to limit the travel of the stopper 18 into the opening 12 by abutting against the lip 32 of the neck 14 when the stopper 18 is fully inserted.

The shield 20 can include a recess 34 configured to receive at least a portion of the stopper 18. The recess 34 of the shield 20 can be at least partially defined by the inner surface 36 of a skirt 38. The skirt 38 can be configured to be positioned outside the generally cylindrical neck 14 when the stopper 18 is seated in the vessel opening 12. In an embodiment illustrated in FIG. 3, the skirt 38 is spaced radially outside the neck 14, providing a generally annular space between the skirt 38 and the neck 14. In an embodiment illustrated in FIG. 3, the stopper 18 is maintained in its seated position in the opening 12 by friction between the neck 14 and the stopper 18. In an embodiment illustrated in FIG. 3, the body portion 26 of the stopper 18 is larger in nominal diameter (when unconfined) than the inner surface 40 of the neck 14, providing an interference fit of the stopper 18 within the neck 14 that presses the stopper 18 into intimate contact with the inner surface 40.

Figure 8:
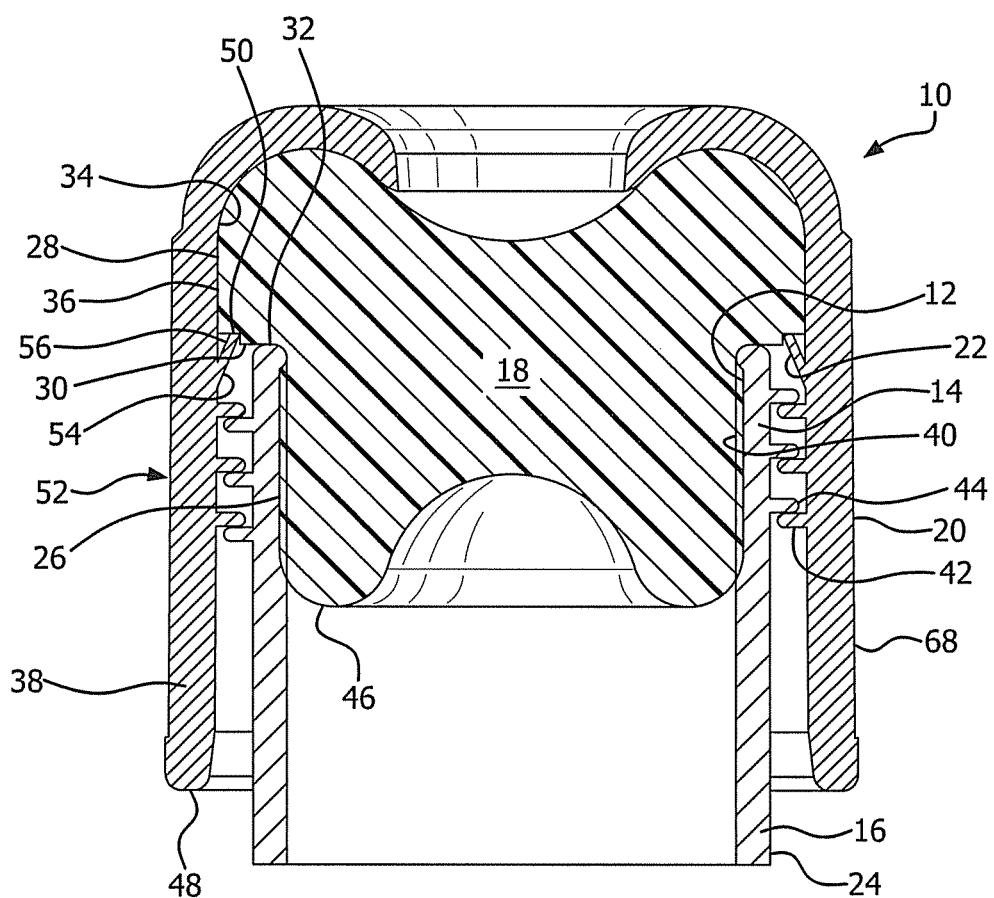
FIG. 8 is a view similar to FIG. 3 of an alternate embodiment of the disclosed technology having a threaded closure for receiving a threaded vessel neck.

As illustrated in FIG. 8, the skirt 38 optionally can be threaded, as with a thread 42, to receive corresponding threads 44 of the neck 14 of a vessel 16. In another embodiment, two, three, four, or more generally parallel helical threads can be provided in the skirt 38 and the neck 14 to allow the shield 20 to be lifted from the neck 14 with relatively few turns, optionally a partial turn, of the skirt 38 with respect to the neck 14. The threaded engagement of the skirt 38 and the neck 14 can provide a mechanical advantage for seating and unseating the stopper 18 in the opening 12 or seating the stopper 18 in the recess 34, though engaged threads might prevent or slow down the operation of removing the stopper 18 by a user holding the vessel 16 in one hand and lifting the stopper by manipulating the shield 20 with the thumb of the same hand. It is contemplated that some users or applications will favor a threaded closure and others will not.

Optionally, the stopper 18 can be recessed into the shield recess. This recessed configuration is illustrated in FIG. 3, showing the lower end 46 of the stopper 18 recessed or spaced into the opening 48 of the shield 20.

The pusher 22 when in use as shown in FIG. 6 can extend radially (i.e. at an angle greater than zero from vertical as shown in FIG. 3) from the inner surface 36 of the skirt 38 into the recess 34 of the shield 20. Alternatively or additionally, the pusher 22 can be configured to extend axially into the recess 34 (i.e. directly or obliquely upward, as shown in FIG. 3). The pusher 22 has a distal portion 50 and a proximal portion 52, with respect to the inner surface 36 of the skirt 38. The proximal portion 52 can be connected to, and as illustrated is integral with, the inner surface 36 of the skirt 38. The distal portion 50 of the pusher 22 can extend axially into the recess 34 (i.e. straight or obliquely upward in the orientation of FIG. 3).

The pusher 22 can be provided in the form of a web 53, illustrated as a generally frustoconical or cone-shaped web having an outer surface 54 facing axially out and an inner surface 56 facing axially in, as illustrated in the Figures. The pusher outer surface 54 optionally can have at least one raised projection 58, or multiple raised projections 58 as shown in FIG. 9, extending out from the surface 54. As illustrated in FIG. 9, the raised projections 58 can be ribs, though they could also be shaped as corrugations, raised compact spots, or provided in other configurations. The projections such as 58 are contemplated to minimize the surface contact area between the head portion 28 of the stopper 18 and the outer surface 54 when the stopper 18 is inserted into the recess 34 when assembling the closure 10. The rib-shaped projections 58 as illustrated also stiffen the pusher 22 in the illustrated embodiment.

Alternatively, the pusher 22 can be one or more, alternatively two or more, circumferentially spaced ribs such as 58 without providing a circumferentially extending web 53 to join them together. The presence of a web 53, however, can function to orient the ribs such as 58, particularly when shifted between their first and second positions as described below.

The distal portion 50 of the pusher 22 engages the abutment 30 of the stopper 18 when the closure 10 is assembled as in FIG. 3. The pusher 22 is configured to push the stopper 18 out of the opening 12 when the shield 20 is withdrawn axially (i.e. moved upward as shown in FIG. 3) from the generally cylindrical neck 14 of the vessel 16, for example when removing the closure 10 from the vessel opening 12. FIG. 6 shows that the pusher 22 can also extend circumferentially within the inner surface 36 of the skirt 38.

The pusher 22 can be movable between a first position, illustrated in FIG. 6, extending axially outward (i.e. the distal portion 50 extending toward the opening 48 vertically or obliquely) from the inner surface 36 of the skirt 38 and a second position, illustrated in FIG. 4, extending axially inward from the inner surface 36 of the skirt 38. The adaptation of the pusher 22 to be movable between the first and second positions is discussed below in connection with the method disclosure.

Method

Another aspect of the invention is a method of making and assembling a closure 10 configured to close the vessel opening 12. The method can be carried out as follows.

A stopper 18, shield 20, and pusher 22 as previously described, or variations upon them, can be provided.

The stopper 18 can be made conventionally, as by injection molding a resilient, injection moldable material. An example of suitable material for the stopper 18 is butyl rubber.

The pusher 22 can be located within, optionally integral with, the shield 20 as previously described. An integral pusher 22 and shield 20 can be made, for example, by injection molding the part 20/22 shown in FIG. 6, using the two-core injection mold shown schematically in FIG. 7. The mold includes a mold cavity 62, an inner core 64, and an outer core 66. The mold cavity 62 can form the exterior 68 of the shield 20. The mostly cylindrical inner core 64 can form the inner surface 56 of the pusher 22 and most of the inner surface 36 of the skirt 38. The mostly annular outer core 66 can form the outer surface 54 of the pusher 22 and the remainder of the inner surface 36 of the skirt 38 lying below the pusher 22 as illustrated in FIG. 7. An example of suitable material for the integral pusher 22 and shield 20 is a copolymer of polyethylene and polypropylene.

In an alternate embodiment, the inner and outer cores 64 and 66 can be integral, defining a one-piece core.

In the first or as-molded position illustrated in FIGS. 6 and 7, the pusher distal portion 50 is in a first position extending axially outward from the inner surface 36 of the skirt 38. The first position of the pusher distal portion 50 is contemplated to facilitate removing the cores 64 and 66, as the removal of the outer core 66 opens a space between the inner core 64 and the just-formed skirt 38. The pusher 22 can then sweep through the space that has been opened and fold against the inner surface 36 of the skirt 38 as the inner core 64 is withdrawn from the cavity 62.

Other core arrangements are also contemplated. If the cores 64 and 66 are integral, the integral core 64/66 can be withdrawn, again folding the distal portion 50 against the inner surface 56 but increasing the surface area of contact between the pusher 22 and the portions of the core 64/66 that form it, compared to a two-part core.

The pusher 22 can alternatively be molded in its second position extending axially inward into the recess 34 of the shield 20. If this is done, however, the withdrawal of the inner core portion forming the portion of the recess 34 above the pusher 22 would tend to invert the pusher 22 to its first position.

Alternatively, the combined shield 20 and pusher 22 can be made by a method such as lost-wax casting that does not require a core to be withdrawn in one piece. Alternatively, more complex cores having outer portions that are withdrawn radially inward after withdrawing an inner portion axially are also contemplated.

Once provided in the first position as described above, either as molded or otherwise, the pusher distal portion 50 can be displaced inward into the recess 34 of the shield 20 to a second position, illustrated for example in FIG. 3, extending axially inward (either obliquely or straight inward) from the inner surface 36 of the skirt 38. The pusher 22 in the first position can be displaced to the second position by inserting a tool 70, as shown in FIG. 9, into the recess 34 and bearing the tool 70 against the outer surface 54 of the pusher 22, inverting the cone defined by the pusher 22 to its second position. The tool 70 can then be withdrawn. Alternatively, the pusher 22 in the first position can be displaced to the second position by inserting the stopper 18 into the recess 34, causing the head portion 28 of the stopper 18 to function in the same manner as the tool 70, except that the stopper 18 can be inserted further into the recess 34 of the shield 20 to a seated position, shown in FIG. 3, after the pusher distal portion 50 is displaced to its second position.

The stopper 18 can be inserted into the opening 12 before or after the stopper 18 is seated in the recess 34.

In operation, when the stopper 18 is seated in the recess 34, the distal portion 50 of the pusher 22 engages the stopper 18 and is positioned to push the stopper 18 out of the opening 12 when the shield 20 is withdrawn axially (moved upward as shown in FIG. 3) from the vessel opening 12.

The disclosed embodiments are not intended to limit the full scope of the invention as defined by the claims.

What is claimed is:

1. A closure for an opening of a generally cylindrical neck of a vessel, the closure comprising:
   a stopper configured to seat at least partially within the opening;
   a shield comprising a recess configured to receive at least a portion of the stopper, the recess being at least partially defined by the inner surface of a skirt configured to be positioned outside the generally cylindrical neck when the stopper is seated in the opening; and
   a pusher extending radially into the recess from the inner surface of the skirt, the pusher having a distal portion, with respect to the inner surface of the skirt, engaging the stopper and configured to push the stopper out of the opening when the shield is withdrawn axially from the generally cylindrical neck, the pusher being movable between a first position extending axially outward from the inner surface of the skirt and a second position extending axially inward from the inner surface of the skirt.

2. The closure of claim 1, in which the stopper comprises:
   a body portion configured to seat at least partially within the opening; and
   a head portion secured to the body portion, the head portion configured to extend at least partially outside the opening when the body portion is seated at least partially within the opening.

3. The closure of claim 2, in which the head portion comprises a stopper abutment extending radially outward from the body portion of the stopper.

4. The closure of claim 3, in which the stopper abutment is a circumferentially extending flange.

5. The closure of claim 1, in which the pusher extends circumferentially within the inner surface of the skirt.

6. The closure of claim 1, in which the pusher has a proximal portion connected to the inner surface of the skirt and a distal portion extending axially into the recess.

7. The closure of claim 1, in which the distal portion of the pusher engages the abutment of the stopper.

8. The closure of claim 1, in which the stopper is recessed into the shield recess.

9. The closure of claim 1, in which the pusher has an outer surface facing axially out and an inner surface facing axially in.

10. The closure of claim 9, in which the pusher outer surface has at least one raised projection extending out from the surface.

11. The closure of claim 1, in which the pusher comprises a generally frustoconical web.

12. The closure of claim 1, in which the pusher is integral with the skirt.

13. The closure of claim 1, in which the skirt is threaded to receive corresponding threads of a generally cylindrical neck of a vessel.

14. A method of assembling a closure configured to close an opening of a generally cylindrical neck of a vessel, the method comprising:
   providing a stopper configured to be seated at least partially within an opening defined by a generally cylindrical neck of a vessel;
   providing a shield comprising a recess configured to at least partially receive the stopper, the recess being at least partially defined by the inner surface of a skirt and having an opening sized to pass at least a portion of the stopper;

providing a pusher within the shield, the pusher having a distal portion extending radially into the recess from the inner surface of the skirt, the pusher distal portion being in a first position extending axially outward from the inner surface of the skirt;

displacing the pusher distal portion to a second position extending axially inward from the inner surface of the skirt; and inserting the stopper into the recess of the shield to a seated position at which the pusher engages the stopper and is positioned to push the stopper out of the opening when the shield is withdrawn axially from a generally cylindrical neck of a vessel.

15. The method of claim 14, in which the pusher in the first position is displaced to the second position by inserting a tool into the recess.

16. The method of claim 14, in which the pusher in the first position is displaced to the second position by inserting the stopper into the recess.

17. The method of claim 14, in which the pusher is integral with the skirt.

18. The method of claim 14, in which the pusher is formed in a single-shot injection mold with a single core.

19. The method of claim 14, in which the pusher is formed in a single-shot injection mold with a double core.

* * * * *